US008654187B2

(12) United States Patent
Mizutani

(10) Patent No.: US 8,654,187 B2
(45) Date of Patent: Feb. 18, 2014

(54) WORK RECOGNITION SYSTEM, WORK RECOGNITION DEVICE, AND WORK RECOGNITION METHOD

(75) Inventor: Kenji Mizutani, Kyoto (JP)

(73) Assignee: Panasonic Corporation, Osaka (JP)

( * ) Notice: Subject to any disclaimer, the term of this patent is extended or adjusted under 35 U.S.C. 154(b) by 306 days.

(21) Appl. No.: 13/056,789

(22) PCT Filed: May 21, 2010

(86) PCT No.: PCT/JP2010/003419
§ 371 (c)(1),
(2), (4) Date: Jan. 31, 2011

(87) PCT Pub. No.: WO2010/143361
PCT Pub. Date: Dec. 16, 2010

(65) Prior Publication Data
US 2011/0128363 A1 Jun. 2, 2011

(30) Foreign Application Priority Data
Jun. 8, 2009 (JP) ................................. 2009-137761

(51) Int. Cl.
*H04N 9/47* (2006.01)
*H04N 7/18* (2006.01)

(52) U.S. Cl.
USPC ......................................................... 348/77

(58) Field of Classification Search
USPC ......................................................... 348/77
See application file for complete search history.

(56) References Cited

U.S. PATENT DOCUMENTS

| 6,215,890 B1 | 4/2001 | Matsuo et al. |
| 6,571,193 B1 | 5/2003 | Unuma et al. |
| 7,768,498 B2 | 8/2010 | Wey |
| 2002/0183961 A1* | 12/2002 | French et al. ................. 702/150 |

(Continued)

FOREIGN PATENT DOCUMENTS

| CN | 1809801 | 7/2006 |
| CN | 1816792 | 8/2006 |

(Continued)

OTHER PUBLICATIONS

International Search Report issued Aug. 31, 2010 in International (PCT) Application No. PCT/JP2010/003419.

(Continued)

*Primary Examiner* — Dave Czekaj
*Assistant Examiner* — Mohammad J Rahman
(74) *Attorney, Agent, or Firm* — Wenderoth, Lind & Ponack, L.L.P.

(57) ABSTRACT

A work recognition device, which recognizes processes in a user's work, includes a whole-state observation time determination unit that determines, as a whole-state observation time, from among observation times of chronological first observation values generated by a first sensor to represent movements of a user's hand, an observation time of observing a first observation value representing a predetermined movement of the hand; and an observation value selection unit that selects a second observation value corresponding to the time determined by the determination unit from among chronological second observation values generated by a second sensor to represent scenes in the user's work. Additionally, a process recognition unit specifies a process in the work, by comparing the second observation value selected by the selection unit to pieces of knowledge data associated with work processes in which the user performs predetermined movements of the hand.

15 Claims, 18 Drawing Sheets

(56) References Cited

U.S. PATENT DOCUMENTS

| | | |
|---|---|---|
| 2003/0208335 A1 | 11/2003 | Unuma et al. |
| 2006/0082546 A1 | 4/2006 | Wey |
| 2006/0093189 A1 | 5/2006 | Kato et al. |
| 2006/0256072 A1 | 11/2006 | Ueshima et al. |
| 2007/0124702 A1 | 5/2007 | Morisaki |
| 2009/0058800 A1 | 3/2009 | Ishigaki et al. |

FOREIGN PATENT DOCUMENTS

| | | |
|---|---|---|
| JP | 8-320920 | 12/1996 |
| JP | 9-44668 | 2/1997 |
| JP | 10-113343 | 5/1998 |
| JP | 11-174948 | 7/1999 |
| JP | 2003-281297 | 10/2003 |
| JP | 2006-133937 | 5/2006 |
| JP | 2006-215680 | 8/2006 |
| JP | 2007-172577 | 7/2007 |
| JP | 2009-059108 | 3/2009 |
| JP | 2009-110038 | 5/2009 |
| WO | 2004/114112 | 12/2004 |

OTHER PUBLICATIONS

Motomu Takano et al., "*Object detection from cooking video by restriction from accompanying text information*", The Annual Conference of the Japanese Society for Artificial Intelligence, 2003.

Partial Translation of Chinese Office Action issued Nov. 1, 2013 in Chinese Application No. 201080003376.8.

\* cited by examiner $$|\alpha(t)| \approx |a(t)| - |g| = \sqrt{|\alpha(t)|^2 + 2|\alpha(t)||g|\cos\theta(t) + |g|^2} - |g|$$

$$\Delta \phi(t) = \cos^{-1} \frac{a(t) \cdot a(t-1)}{|a(t)| \, |a(t-1)|}$$

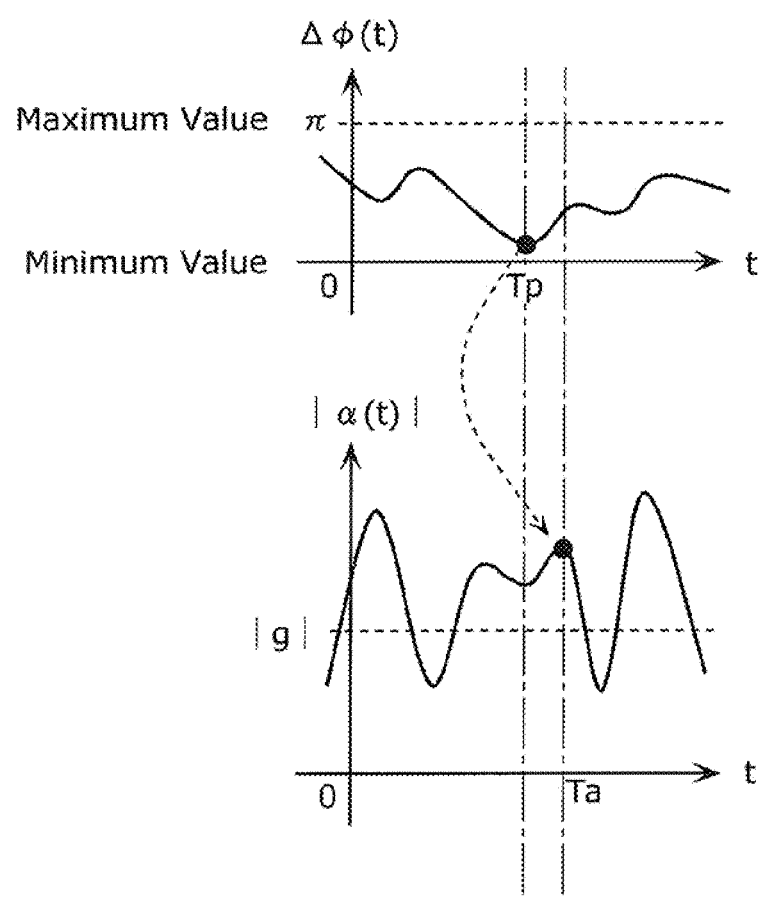

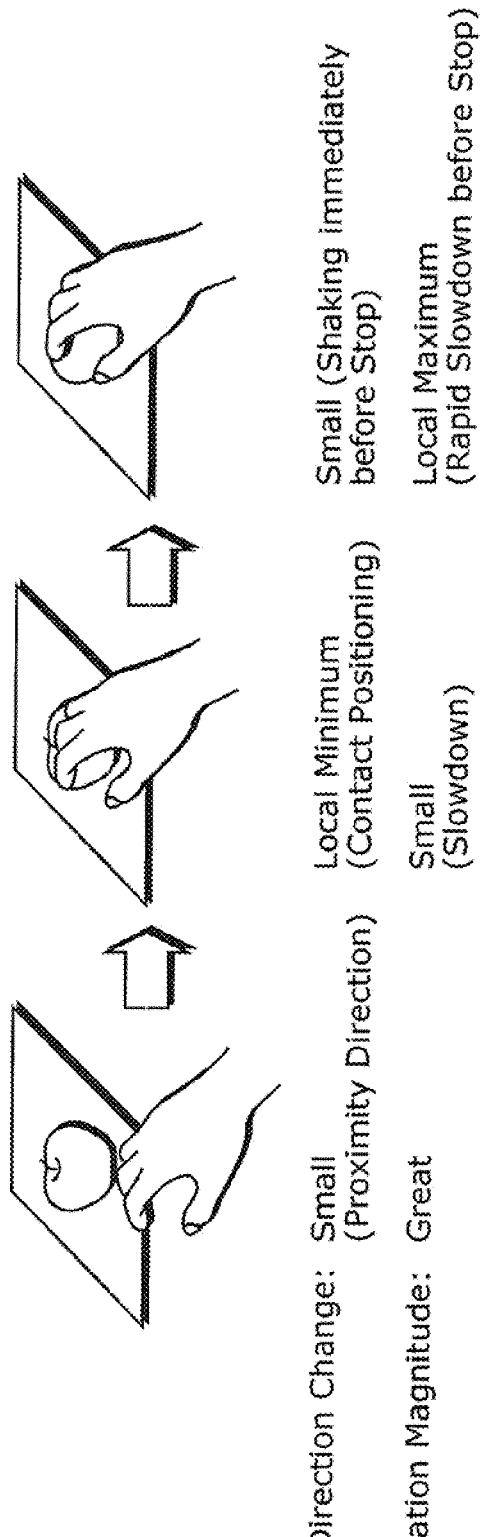

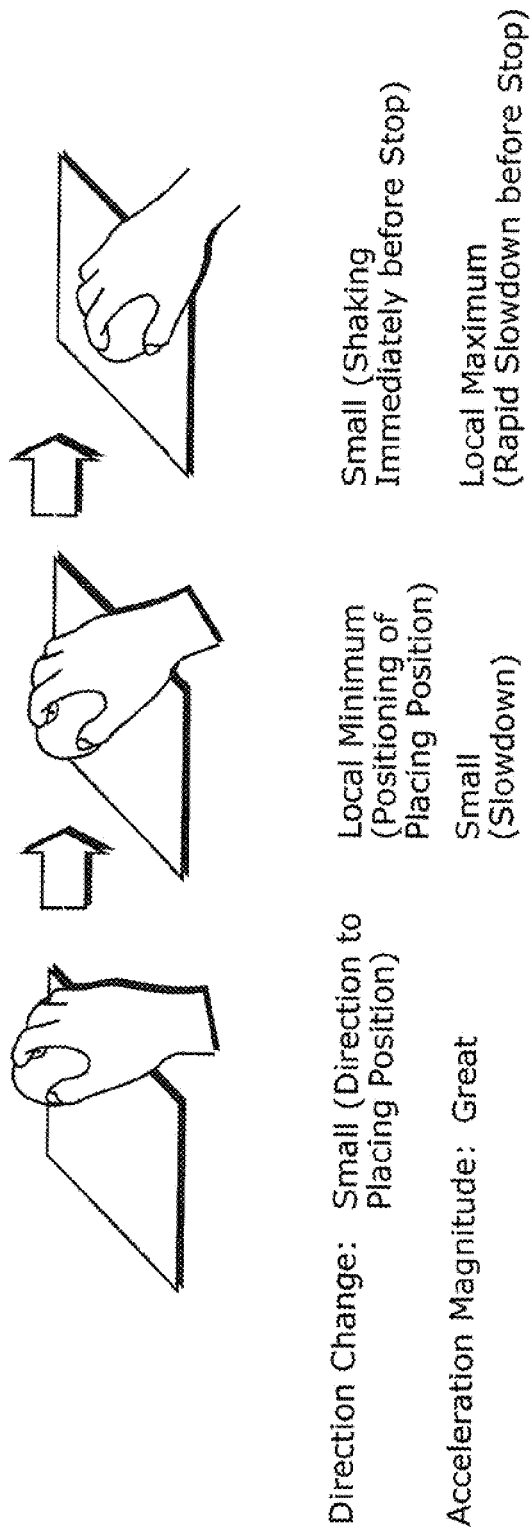

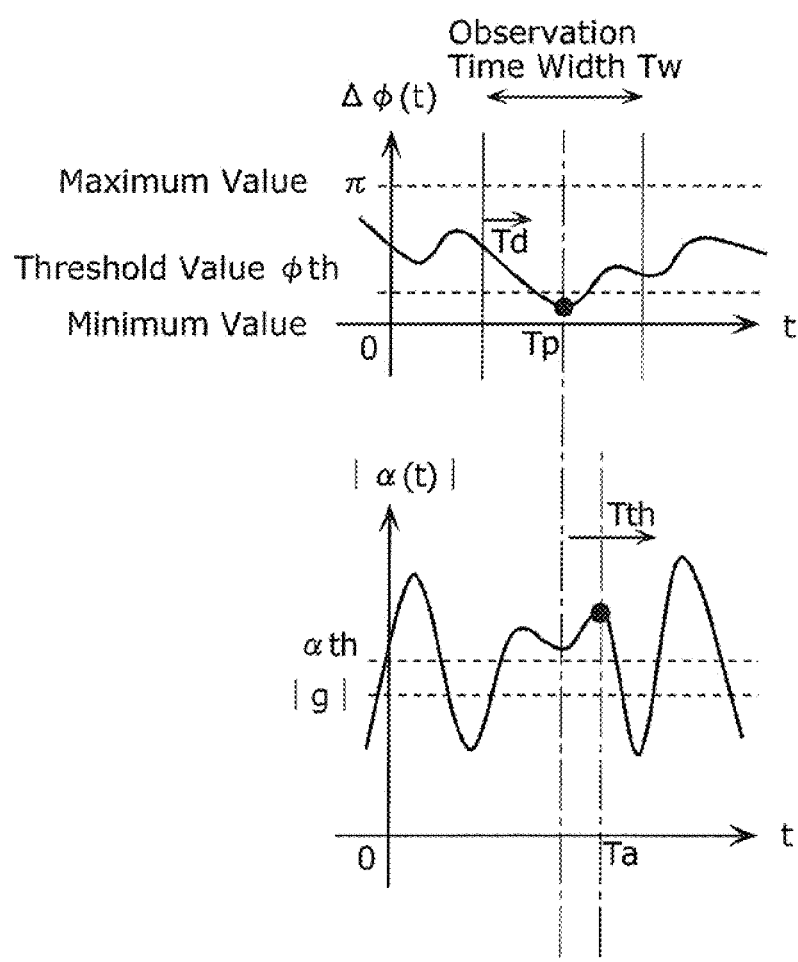

WORK RECOGNITION SYSTEM, WORK RECOGNITION DEVICE, AND WORK RECOGNITION METHOD

BACKGROUND OF INVENTION

1. Technical Field

The present invention relates to work recognition systems and work recognition devices which recognize respective processes in work performed by a person, based on previously-learned knowledge such as image features.

2. Background Art

In recent years, work recognition systems have been getting developed to recognize processes in work performed by a person using hands, such as cooking, cleaning, and laundry in daily life, by observing states (scenes) and/or movements in the work by sensors such as cameras. Such work recognition systems previously learn, off-line, objects that are targets of work, or features of human work actions (processes), so as to accumulate them as pieces of knowledge data. Then, the work recognition systems compare the pieces of knowledge data to observation values generated by the sensors to recognize the objects or actions (processes). The recognition results are used as various triggers for information provision devices to present a next work process or warn a danger caused by the work process. Or, the recognition results are used as inputs of devices that utilize daily actions as log data. For example, Non-Patent Reference 1 discloses a system that recognizes processes in hand work as cooking, by using foods such vegetables and meat as target objects.

FIG. 18 shows a summary of processing performed by the system disclosed in Non-Patent Reference 1 to recognize processes in hand work of a person. First, a designer of the system adds, off-line, a closed caption 102 corresponding to a subtitle for explaining a cooking process, to an image 101 of a cooking scene which is captured by a camera. Next, once more off-line, the system receives the image 101 and the closed caption 102 as inputs. The system compares the image 101 to previously-learned pieces of knowledge data regarding a time at which a text is obtained from the closed caption 102, so as to specify a target object in the work process.

PRIOR ARTS

Non-Patent References
Non-Patent Reference 1: "Object detection from cooking video by restriction from accompanying text information", Takano, et al., The Annual Conference of the Japanese Society for Artificial Intelligence, 2003 (page 1, FIG. 2)

SUMMARY OF INVENTION

However, in order to structure a device capable of responding to respective human work processes in real time, all the human work processes should be recognized on-line. For example, in the case of a cooking guide system or the like, it is necessary to present video or audio of a next cooking work process immediately after completion of a current cocking work process. Therefore, in real-time processing, the system disclosed in Non-Patent Reference 1 cannot prepare a closed caption 102 to reduce calculation processing consumed to evaluate knowledge. Therefore, the conventional system needs to compare each of images sampled at regular time intervals, to pieces of knowledge data. Such comparison processing requires a huge calculation amount increased in proportion to a frame rate or resolution of the image or quality or an amount of the knowledge data. As a result, the real-time processing is significantly deteriorated. In addition, if the knowledge data uses changes of images with respect to time to indicate features of work process, there is a possibility that a time width of the work process is decreased or increased. The comparison to the knowledge data needs to be performed in consideration of the time width increase/decrease. As a result, the calculation amount is further increased.

In order to address the above problems, an object of the present invention is to provide a work recognition system or the like that can recognize respective processes in work performed by a user in real time.

In accordance with an aspect of the present invention for achieving the object, there is provided a work recognition device including: a whole-state observation time determination unit configured to determine, as a whole-state observation time, from among observation times of a plurality of first observation values generated by a speed sensor to represent respective movements of a hand of a user in chronological order, an observation time of observing a first observation value representing a predetermined movement of the hand, based on magnitudes of the plurality of first observation values and an angular difference between the plurality of first observation values; and an observation value selection unit configured to select a second observation value corresponding to the whole-state observation time determined by the whole-state observation time determination unit, from among a plurality of second observation values generated by an imaging unit to represent respective states in work of the user in chronological order.

With the above structure, it is possible to evaluate knowledge regarding a part of the second observation values generated by the imaging unit, and thereby recognize a process in the work. Thereby, it is possible to narrow down a range of the second observation values to be used to evaluate the knowledge data. A calculation amount required to recognize processes in the work can be therefore reduced. As a result, it is possible to recognize processes in the work performed by the user in real time. In addition, preparation such as closed caption generation is not necessary to calculate the whole-state observation time.

It should be noted that the present invention can be implemented not only as the work recognition device including the above-described characteristic units, but also as a work recognition method including steps performed by the characteristic units included in the work recognition device. The prevent invention can be implemented further as a program causing a computer to execute the characteristic steps included in the work recognition method. Of course, the program can be distributed via a computer-readable recording medium such as a Compact Disc-Read Only Memory (CD-ROM) or via a communication network such as the Internet.

According to the present invention, a calculation amount required to evaluate knowledge is significantly reduced so as to recognize processes in work at a high speed. At the same time, electrical power required for unnecessary calculation can be reduced. Thereby, the present invention can recognize processes in work performed by a user in real time.

BRIEF DESCRIPTION OF DRAWINGS

FIG. 7 is a graph schematically showing an operation performed by the time determination unit according to the first embodiment of the present invention.

FIG. 8A is a diagram showing changes of an acceleration magnitude and a direction of a hand when a user picks up an object by the hand.

FIG. 8B is a diagram showing changes of an acceleration magnitude and a direction of the hand when a user puts down an object by the hand.

FIG. 9 is a graph schematically showing a method of determining a whole-state observation time by the time determination unit according to the first embodiment of the present invention.

DETAILED DESCRIPTION OF INVENTION

The following describes embodiments according to the present invention with reference to the drawings.

The below-described embodiments provide systems that obtain in real time, from images in which a user is cooking, an user's action corresponding to a closed caption, or a target object of the user's action. In the above situation, the below-described embodiments can efficiently observe only a featured image from among images of a process in cooking. With the above structure, the system does not need to evaluate all of the images, thereby increasing a processing speed. As a result, the system can extract the user's action or the object promptly.

First Embodiment

Figure 1:
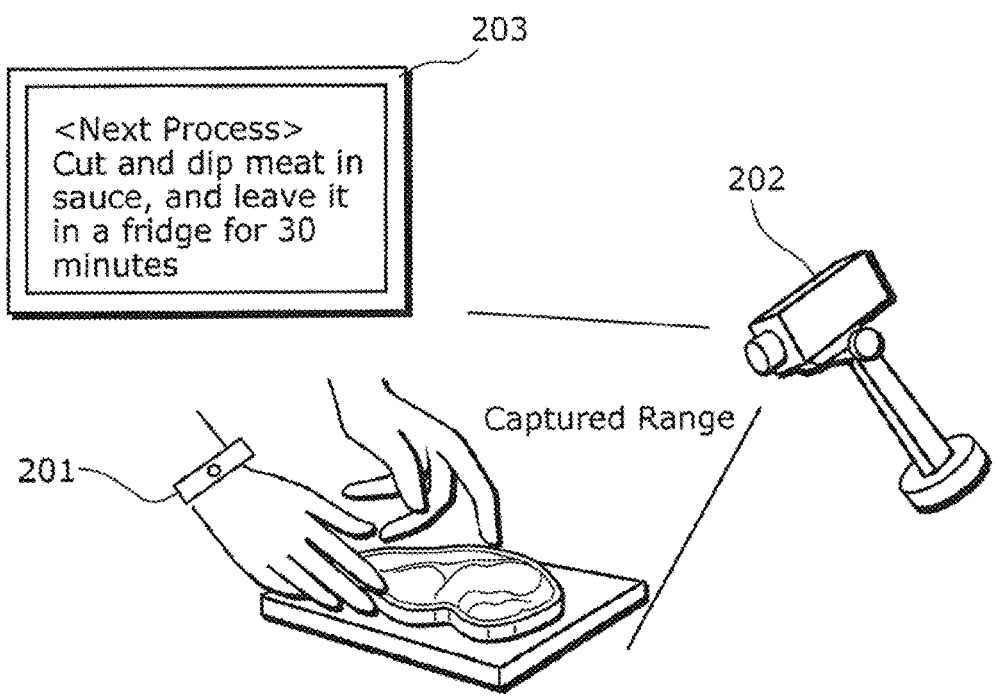
FIG. 1 is a diagram showing an application of a hand work recognition device according to a first embodiment of the present invention.

FIG. 1 shows an application of the present invention in actual hand work recognition. In FIG. 1, a second sensor 202 captures an image of a state (scene) where a user is cooking. An hand work recognition device recognizes a process in the cooking (here, a process of placing meat on a chopping board). After that, the hand work recognition device presents the user with video of a next process (a process for cutting and dipping meat in sauce, and leaving it in a fridge for 30 minutes). In FIG. 1, the user wears a first sensor 201 including an acceleration sensor at his/her dominant hand. The second sensor 202 is a camera that captures a whole state (scene) of the user's work movement. A recognition result of the hand work recognition device is used as a trigger of processing performed by an information provision device 203 that provides various information such as presentation of a next work process or warning of danger that would be caused by the work process.

Figure 2:
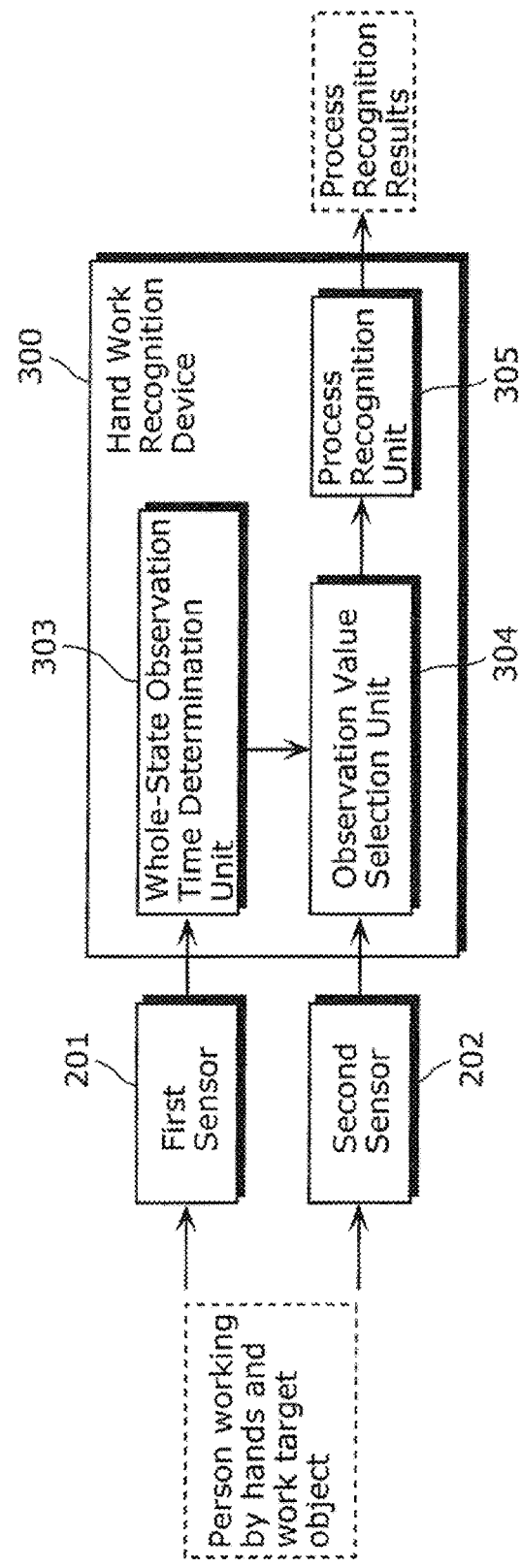
FIG. 2 is a functional block diagram of the hand work recognition device according to the first embodiment of the present invention.

FIG. 2 is a functional block diagram of a structure of the hand work recognition device according to the first embodiment of the present invention.

The hand work recognition system is a system that recognizes processes in hand work performed by a user. The hand work recognition system includes the first sensor 201, the second sensor 202, and a hand work recognition device 300.

The hand work recognition device 300 is a device that recognizes processes in hand work of the user based on observation values generated by the first sensor 201 and the second sensor 202.

The first sensor 201 observes movements of a hand of the user performing hand work, thereby generating first observation values representing the respective movements in chronological order. The second sensor 202 observes scenes (states) of the hand work, thereby generating second observation values representing the respective scenes in chronological order.

The hand work recognition device 300 recognizes processes in the hand work based on the chronological first observation values and the chronological second observation values. The hand work recognition device 300 includes a whole-state observation time determination unit 303, and an observation value selection unit 304, and a process recognition unit 305.

The whole-state observation time determination unit 303 determines an observation time of a first observation value representing a predetermined movement of the user's hand (hereinafter, referred to as a "whole-state observation time") based on the chronological first observation values.

The observation value selection unit 304 selects a second observation value associated with the whole-state observation time determined by the whole-state observation time determination unit 303.

The process recognition unit 305 specifies a process in the user's hand work of the user, by comparing a second observation value selected by the observation value selection unit 304 to pieces of knowledge data associated with respective hand work processes of the user in each of which the user performs a corresponding predetermined movement. The process recognition unit 305 includes a known recognition unit as disclosed in Non-Patent Reference 1. More specifically, in order to recognize each user's hand work process, the process recognition unit 305 calculates a relevance between a selected second observation value and the previously-learned pieces of knowledge data of image features. Thereby, the process recognition unit 305 determines, as a hand work process, a hand work process associated with a piece of knowledge data to which the second observation value is most relevant. The process recognition unit 305 outputs the determined hand work process as a recognition result.

Next, an example of the knowledge data is explained. For example, if the user's hand work is cooking, colors of foods feature processes in the hand work. By learning color distribution of image data, the knowledge data can be generated. For instance, a piece of knowledge data is generated to indicate that color distribution of image data includes many red regions if a food is a tomato. Cooking is featured by a temporal change of food color. Therefore, it is also possible to generate knowledge data by learning a temporal change of color distribution of image data in chronological order. For example, another piece of the knowledge data is generated to indicate that white regions are gradually increased over time in color distribution of image data when an onion is being finely chopped. By determining a piece of knowledge data to which a target selected second observation value corresponds, it is possible to specify a process in the user's hand work.

Figure 3:
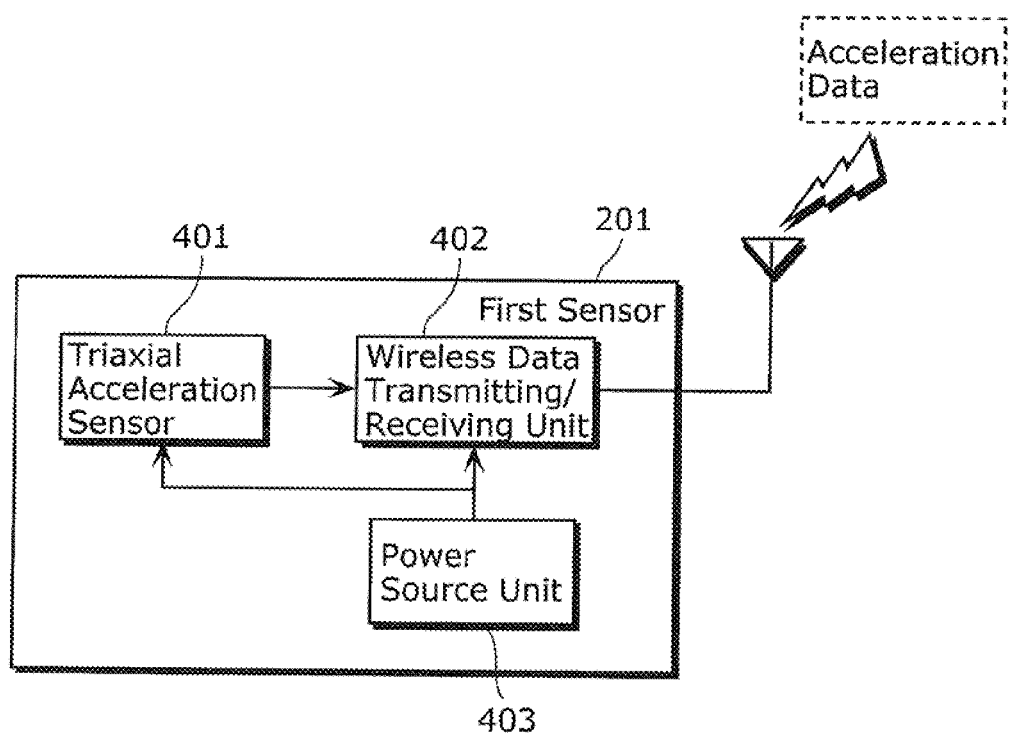
FIG. 3 is a block diagram of a first sensor in the hand work recognition device according to the first embodiment of the present invention.

FIG. 3 shows a structure of the first sensor 201. The first sensor 201 includes a triaxial acceleration sensor 401, a wireless data transmitting/receiving unit 402, and a power source unit 403.

The triaxial acceleration sensor 401 is a small semiconductor acceleration meter manufactured using the Micro Electro Mechanical Systems (MEMS) technology. The triaxial acceleration sensor 401 has standard specifications capable of measuring an acceleration of approximately ±3 G (where G denotes a gravity acceleration) for three axises x, y, and z. The triaxial acceleration sensor 401 also has specifications of outputting data of approximately 40 samples per second.

The wireless data transmitting/receiving unit 402 transmits, in real time, observation values (the above-described first observation values) to the whole-state observation time determination unit 303 of the hand work recognition device 300. Here, the wireless data transmitting/receiving unit 402 transmits the observation values to the whole-state observation time determination unit 303, using a wireless data transmission standard such as Bluetooth™ serial port profile.

The power source unit 403 is a disposable primary cell or a rechargeable secondary battery, which supplies necessary power to the triaxial acceleration sensor 401 and the wireless data transmitting/receiving unit 402 to be operated.

The first sensor 201 has a size by which a person can wear the first sensor 201 on his/her arm as shown in FIG. 1. The first sensor 201 is attached to the arm to sensitively react movements of the arm.

Figure 4:
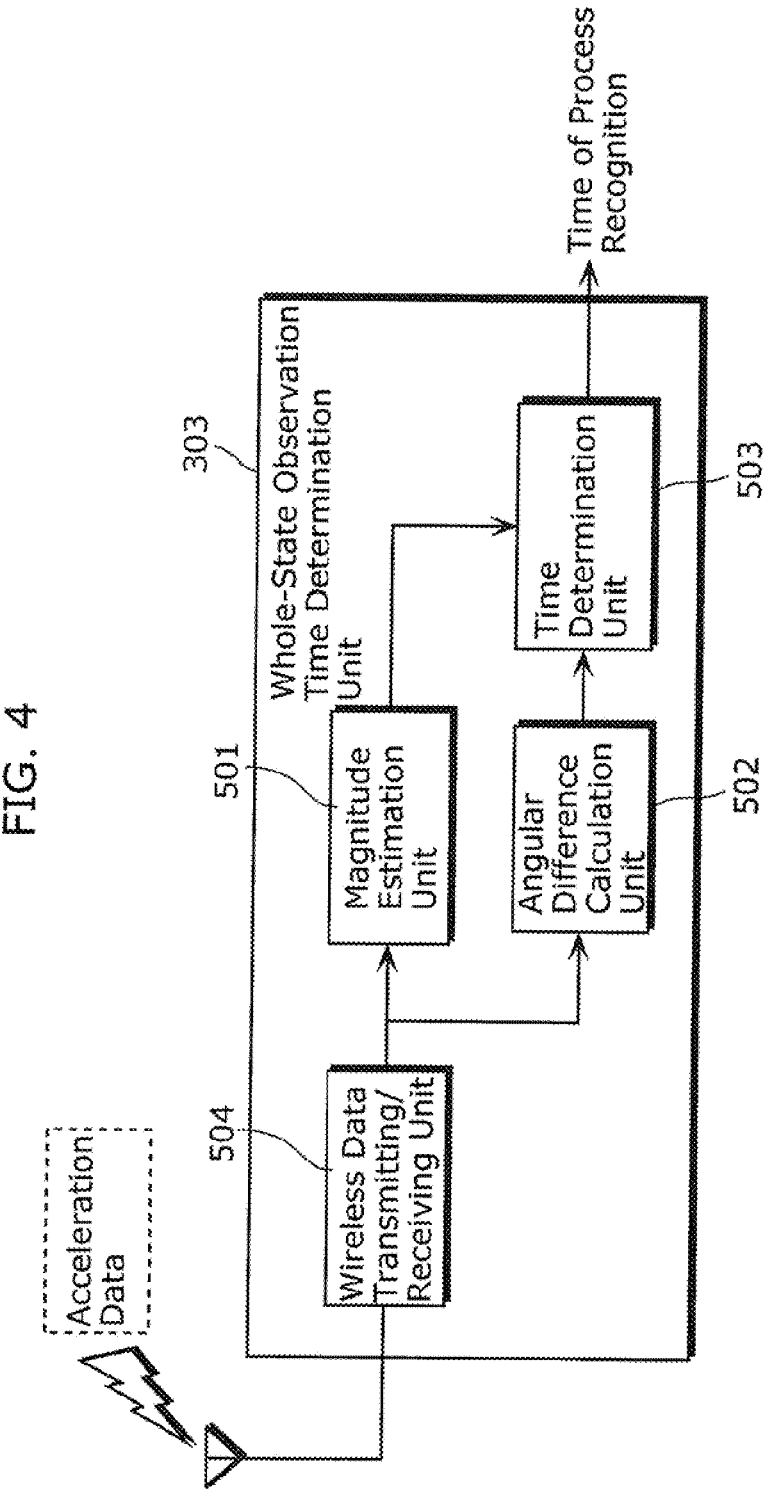
FIG. 4 is a block diagram of the inside of a whole-state observation time determination unit according to the first embodiment of the present invention.

FIG. 4 shows an inside structure of the whole-state observation time determination unit 303. The whole-state observation time determination unit 303 includes a wireless data transmitting/receiving unit 504, a magnitude estimation unit 501, an angular difference calculation unit 502, and a time determination unit 503.

The wireless data transmitting/receiving unit 504 receives, from the wireless data transmitting/receiving unit 402, accelerations a(t) that are observation values detected by the triaxial acceleration sensor 401.

Figures 5A, 5B:
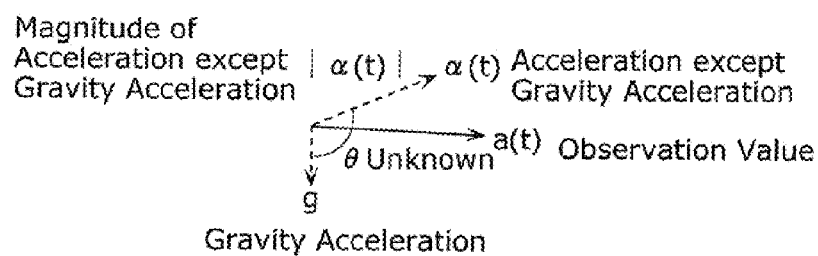
FIG. 5A is a diagram showing a relationship between an acceleration a(t) and a gravity acceleration g.
FIG. 5B is a diagram showing an approximation expression of a magnitude |α(t)| of an acceleration except a gravity acceleration, which is used by a magnitude estimation unit according to the first embodiment of the present invention.

The magnitude estimation unit 501 estimates a magnitude |α(t)| of an acceleration α(t) that is obtained by subtracting a gravity acceleration g from each of the accelerations a(t) received by the wireless data transmitting/receiving unit 504. In general, the acceleration meter (the triaxial acceleration sensor 401) is influenced by a gravity. Therefore, as shown in FIG. 5A, an acceleration a(t) measured by the acceleration meter is a vector sum of: a gravity acceleration g; and an acceleration α(t) that does not include the gravity acceleration g. If an attitude of the acceleration meter is unknown, an angle θ between a gravity acceleration g and an acceleration except the gravity acceleration g is unknown. Therefore, it is impossible to correctly eliminate components of the gravity acceleration. In the first embodiment, |α(t)| is approximated by a calculation expression shown in FIG. 5B, and thereby used as a magnitude of the acceleration α(t) from which the gravity acceleration g is eliminated.

Figures 6A, 6B:
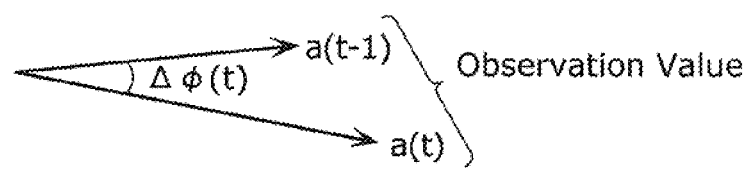
FIG. 6A is a diagram for explaining an angular difference.
FIG. 6B is a diagram for showing a calculation expression of an angular difference, which is used by an angular difference calculation unit according to the first embodiment of the present invention.

For each of the accelerations a(t) including the gravity acceleration which are detected by the triaxial acceleration sensor 401, the angular difference calculation unit 502 calculates an angle between the target acceleration a(t) and an acceleration a(t−1) that is detected at a time close to a time of the acceleration a(t). More specifically, as shown in FIG. 6A, the angular difference calculation unit 502 calculates an angle (where a minimum value is 0, a maximum value is π, and a unit is radian) between: an acceleration a(t) at a target measurement time t; and an acceleration a(t−1) at a measurement time (t−1) immediately prior to the measurement time (t). In short, the angular difference calculation unit 502 calculates a difference between the angles (angular difference) Δφ(t) according to a calculation expression shown in FIG. 6B.

The time determination unit 503 determines, as a whole-state observation time, a measurement time t satisfying predetermined conditions in the calculation of angular differences Δφ(t). Here, the predetermined conditions are the situation where the magnitude |α(t)| of the acceleration α(t) except the gravity acceleration g which is estimated by the magnitude estimation unit 501, and the angular difference Δφ(t) calculated by the angular difference calculation unit 502 show a predetermined pattern. As described above, a second observation value at the determined whole-state observation time is selected by the observation value selection unit 304.

When a person does hand work carefully, the person shows movement features in which the person puts down a holding object after stabilizing a direction of a holding hand, or picks up a placed object by a hand after stabilizing a direction of the hand. In other words, an acceleration of the hand dramatically changes after stabilization of an attitude of the hand. The time determination unit 503 uses the above features to determine whole-state observation times. More specifically, the time determination unit 503 determines, as a whole-state observation time, a time Tp at which an angular difference Δφ(t) calculated by the angular difference calculation unit 502 approaches asymptotically to 0 degree, if, as shown in FIG. 7, a acceleration magnitude |α(t)| estimated by the magnitude estimation unit 501 reaches locally maximum (local maximum at a time Ta in FIG. 7) within a predetermined maximum local maximum value reach time period Tth immediately after the time Tp. In the above processing, picking up of an object by a hand is recognized by focusing on that an acceleration magnitude and a direction of the hand are changed as shown in FIG. 8A. On the other hand, putting down of an object by a hand is recognized by focusing on that an acceleration magnitude and a direction of the hand are changed as shown in FIG. 8B.

A practical method of determining a whole-state observation time is described with reference to FIG. 9. The time determination unit 503 shifts a predetermined observation time width Tw in a time axis direction, overlapping the observation time widths Tw each other. Thereby, the time determination unit 503 sequentially samples values of angular differences $\Delta\phi(t)$ included in the respective observation time widths Tw. The time determination unit 503 determines, as the time Tp, an observation time having a local minimum value among the angular differences $\Delta\phi(t)$, if, within a target observation time width Tw, a time period, during which values of the angular differences $\Delta\phi(t)$ are continuously decreased from a start time of the observation time width Tw, exceeds a predetermined minimum decrease time period Td, and the local minimum value among the angular differences $\Delta\phi(t)$ is equal to or smaller than a predetermined threshold value $\phi$th. Then, the time determination unit 503 outputs the determined time Tp as a whole-state observation time, if a time period from the time Tp to an observation time Ta of a local maximum value of $|\alpha(t)|$ immediately after the time Tp is equal to or shorter than the predetermined maximum local maximum value reach time period Tth, and the local maximum value of $|\alpha(t)|$ exceeds a predetermined threshold value $\alpha$th. In other words, when $|\alpha(t)|$ continues increasing or decreasing in the maximum local maximum value reach time period Tth, the time determination unit 503 does not output any whole-state observation time. On the other hand, when Ta−Tp≤Tth and $|\alpha(Ta)|\le\alpha$th regarding the time Ta at which $|\alpha(Ta)|$ first starts decreasing after increase from the time Tp, the time determination unit 503 outputs the time Tp as a whole-state observation time.

The above-described constants and threshold values, namely, the minimum decrease time period Td, the threshold value $\phi$th, the maximum local maximum value reach time period Tth, and the threshold value $\alpha$th, are determined by observing actual work processes and adjusting these values to obtain appropriate results. A part of these threshold values may be eliminated. For example, the determination using the threshold value $\alpha$th can be eliminated.

The second sensor 202 is a camera that captures video. For example, the second sensor 202 has specifications of generating approximately 30 color still pictures per second and outputting them as the above-described second observation values.

Figure 10:
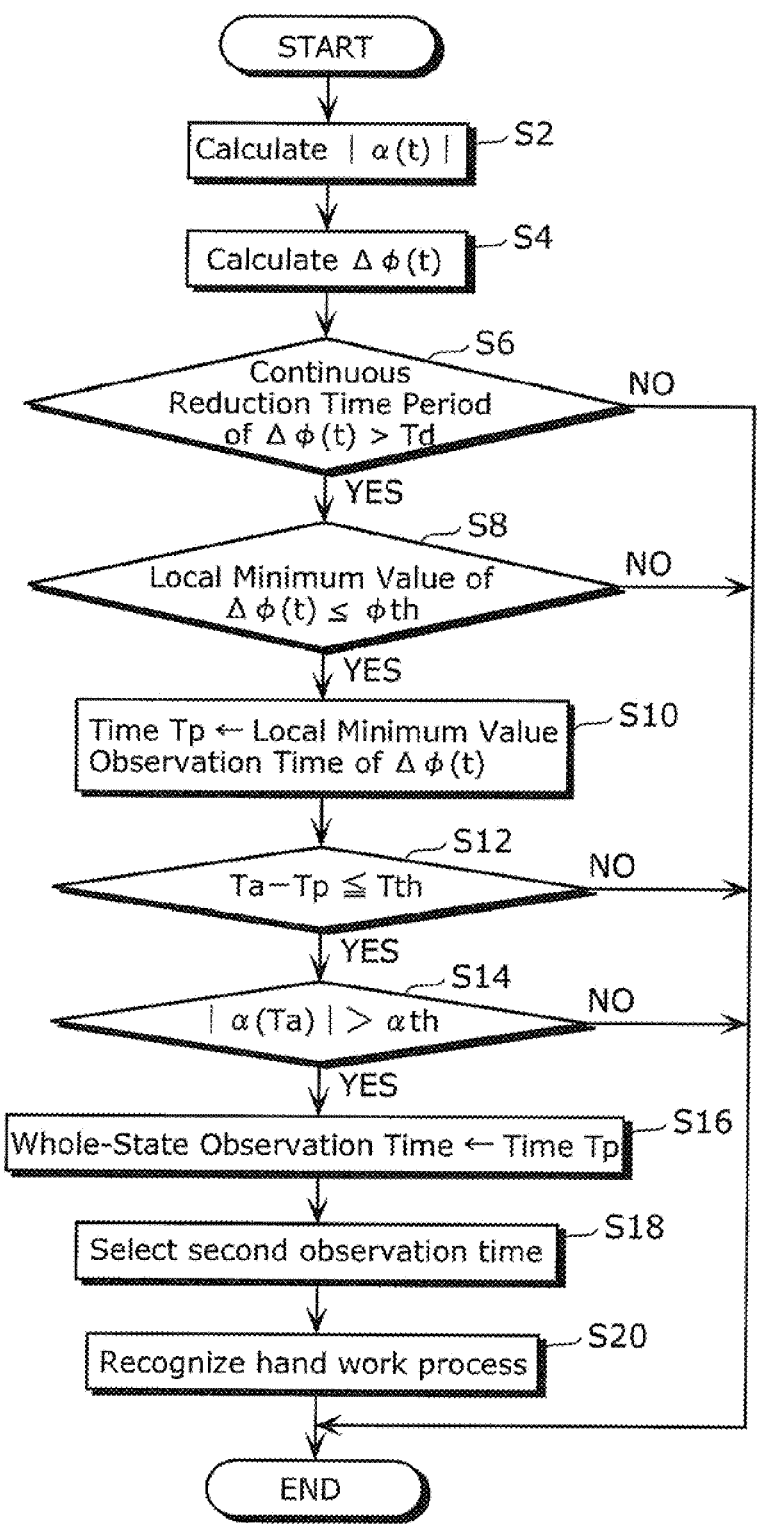
FIG. 10 is a flowchart of processing performed by the hand work recognition device according to the first embodiment of the present invention.

The following describes a flow of the processing performed by the hand work recognition device in the hand work recognition system having the above structure with reference to FIG. 10.

The magnitude estimation unit 501 estimates a magnitude $|\alpha(t)|$ of an acceleration $\alpha(t)$ that is calculated by subtracting the gravity acceleration g from each of the accelerations a(t) received by the wireless data transmitting/receiving unit 504 (S2). Sequentially, the magnitude estimation unit 501 estimates $|\alpha(t)|$ for respective measurement times t.

The angular difference calculation unit 502 calculates an angle (angular difference $\Delta\phi(t)$) between: an acceleration a(t) at a target measurement time t; and an acceleration a(t−1) at a measurement time (t−1) immediately prior to the measurement time (t) (S4). Sequentially, the angular difference calculation unit 502 calculates angular differences $\Delta\phi(t)$ for respective measurement times t (S4).

The time determination unit 503 determines a whole-state observation time, by performing steps S6 to S16 described below using the magnitudes $|\alpha(t)|$ of the respective accelerations $\alpha(t)$ and the angular differences $\Delta\phi(t)$ which are sequentially calculated at steps S2 and S4.

More specifically, the time determination unit 503 determines, as shown in FIG. 9, whether or not, within a target observation time width Tw, a time period, during which values of the angular difference $\Delta\phi(t)$ are continuously decreased from a start time of the observation time width Tw, exceeds the predetermined minimum decrease time period Td (S6).

If the time period exceeds the minimum decrease time period Td (YES at S6), then the time determination unit 503 further determines whether or not a local minimum value among the angular differences $\Delta\phi(t)$ in the observation time width Tw is equal to or smaller than the threshold value $\phi$th (S8).

If the local minimum value among the angular differences $\Delta\phi(t)$ is equal to or smaller than the threshold value $\phi$th (YES at S8), then the time determination unit 503 determines, as a time Tp, an observation time having the local minimum value among the angular differences $\Delta\phi(t)$ (S10).

After step S10, the time determination unit 503 determines whether or not a time period from the time Tp to an observation time Ta of a local maximum value of $|\alpha(t)|$ immediately after the time Tp is equal to or shorter than the predetermined maximum local maximum value reach time period Tth (S12).

If the time period is equal to or shorter than the predetermined maximum local maximum value reach time period Tth (YES at S12), then the time determination unit 503 further determines whether or not the local maximum value of $|\alpha(t)|$ exceeds the predetermined threshold value $\alpha$th (S14).

If the local maximum value of $|\alpha(t)|$ exceeds the threshold value $\alpha$th (YES at S14), the time determination unit 503 finally determines the time Tp as a whole-state observation time to be outputted (S16).

Figure 11:
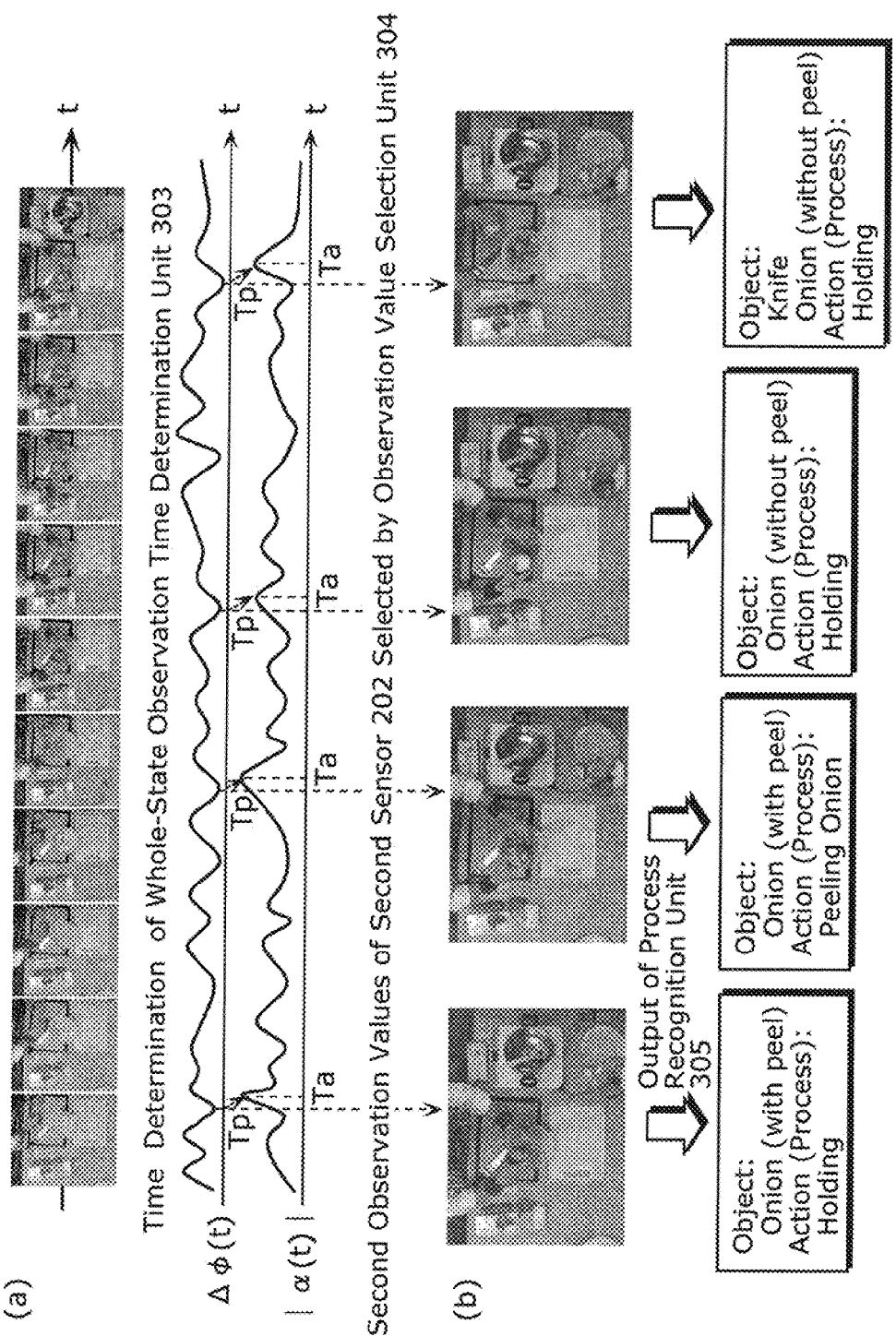
FIG. 11 is a diagram for explaining selection of the second observation value by an observation value selection unit according to the first embodiment of the present invention.

The observation value selection unit 304 selects a second observation value generated at the whole-state observation time Tp by the second sensor 202 (S18). By the above flow, images as shown in (b) in FIG. 11 are selected from images as shown in (a) in FIG. 11 which are generated by the second sensor 202.

Figure 12:
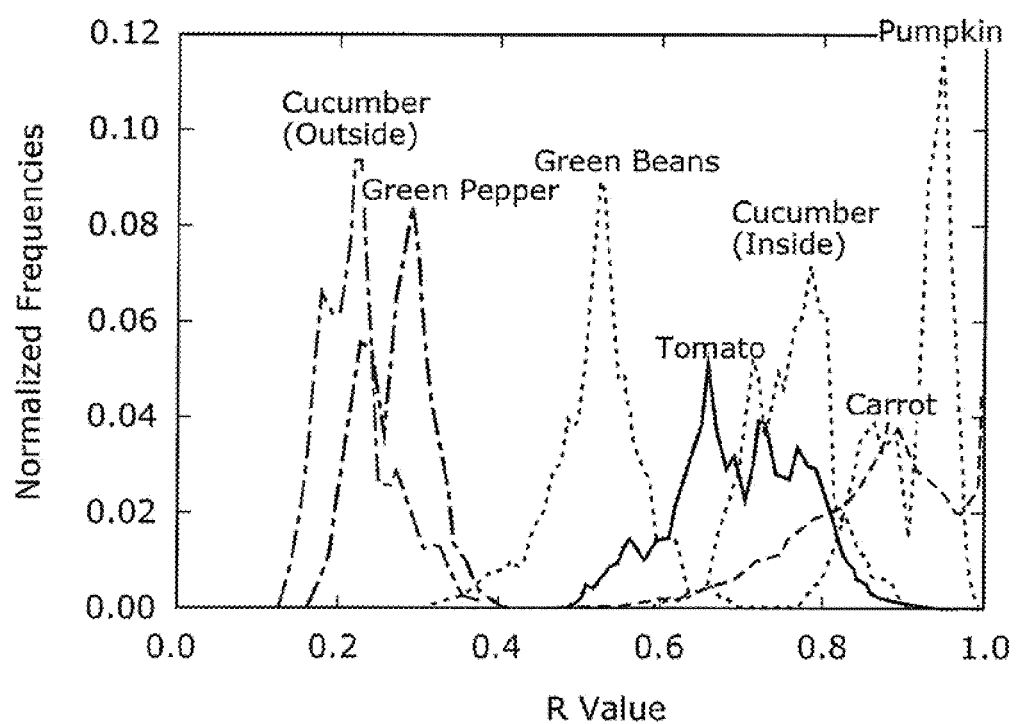
FIG. 12 is a graph showing an example of data related to colors of foods according to the first embodiment of the present invention.

The process recognition unit 305 specifies a process in the user's hand work performed by the user, by comparing each of the second observation values selected by the observation value selection unit 304 to pieces of knowledge data associated with various processes in the user's hand work (S20). For example, data related to food colors shown in FIG. 12 is prepared as the knowledge data. An object in the current hand work process is specified by comparing color distribution of pixels of an image that is a second observation value selected by the observation value selection unit 304 as shown in (b) in FIG. 11, to the knowledge data. In FIG. 12, a horizontal axis represents a value of red components in pixels, and a vertical axis represents normalized frequencies. It is also possible to prepare, as the knowledge data, color data for more detailed objects, such as a "peeled onion" and an "onion with peels". It is further possible to prepare also color distribution regarding colors of a human hand. Thereby, the knowledge data further includes data of structures of pixels constituting shapes of actions (processes) of a human hand ("holding", "peeling", and the like). The knowledge data is used to specify an action of the user as shown in (b) in FIG. 11. For example, the second observation value on the far left in (b) in FIG. 11 is compared to the above-described knowledge data, so that the object is recognized as an "onion" and the action (process) is recognized as "holding" to be outputted.

Referring back to the flowchart of FIG. 10, if the time period, during which values of the angular differences $\Delta\phi(t)$ are continuously decreased, is equal to or shorter than the minimum decrease time period Td (NO at S6), any whole-state observation time is not calculated and the processing is terminated. Likewise, if a local minimum value among the angular differences $\Delta\phi(t)$ is greater than the threshold value $\phi$th (NO at S8), any whole-state observation time is not calculated and the processing is terminated. Also, if the time period from the time Tp to the time Ta is longer than the maximum local maximum value reach time period Tth (NO at S12), any whole-state observation time is not calculated and the processing is terminated. Furthermore, if the local maximum value of |α(t)| is equal to or smaller than the threshold value αth (NO at S14), any whole-state observation time is not calculated and the processing is terminated.

The above-described processing from S6 to S20 is repeated, while shifting a target observation time width Tw shown in FIG. 9 in a time axis direction.

With the above structure, as shown in (a) in FIG. 11, the second sensor 202 outputs consecutive second observation values. On the other hand, according to each of the whole-state observation times Tp determined by the whole-state observation time determination unit 303, the observation value selection unit 304 selects a second observation value to be an input of the process recognition unit 305 as shown in (b) in FIG. 11. The whole-state observation time determination unit 303 determines each of the whole-state observation times Tp in real time by the above-described processing based on changes of an angular difference Δϕ(t) and an acceleration magnitude |α(t)|. Thereby, when the user carefully performs hand work such as cooking, cleaning, and laundry in daily life, it is possible to extract only a second observation value(s) having a high possibility of occurring at a boundary between work processes, such as a start, an end, or a turning point of an action of a user's hand.

The process recognition unit 305 calculates, only for a received second observation value(s), a relevance between the second observation value (image, for example) and pieces of knowledge data regarding image features which are previously learned from respective processes in the user's hand work. Then, the process recognition unit 305 determines, as a hand work process, a hand work process of a piece of the knowledge data to which a target second observation value is most related. The process recognition unit 305 outputs the determined hand work process as a recognition result. Therefore, the process recognition unit 305 evaluates a part of all second observation values which are generated by the second sensor 202, which makes it possible to significantly reduce a calculation amount required to evaluate the learned knowledge for each input observation value. As a result, it is possible to increase a processing speed, and thereby extracting a user's action or an object promptly.

Second Embodiment

The hand work recognition system according to the second embodiment differs from the hand work recognition system according to the first embodiment, in a method of determining a whole-state observation time by the time determination unit 503. Except the above difference, the second embodiment is the same as the first embodiment. Therefore, the details are not repeated in the second embodiment.

Figure 13:
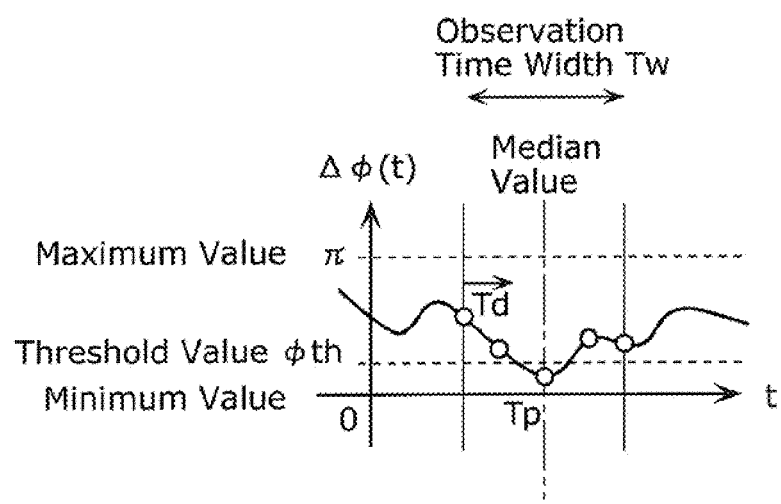
FIG. 13 is a graph showing an example of a positive example of how to cause a learning machine included in a time determination unit to learn according to a second embodiment of the present invention.
Figure 14:
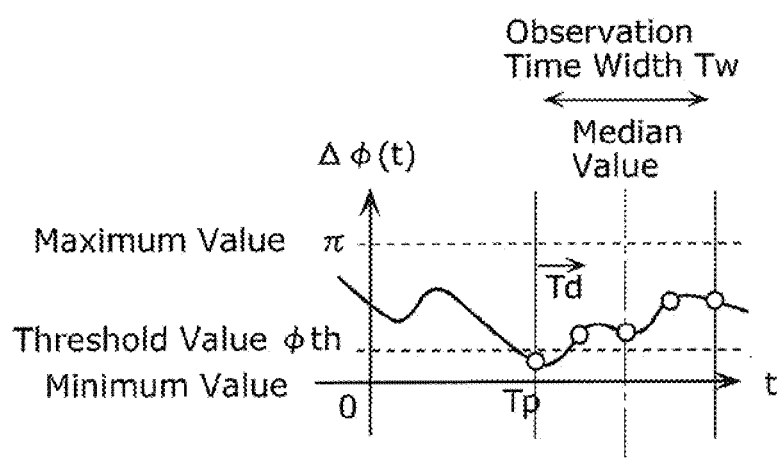
FIG. 14 is a graph showing an example of a negative example of how to cause the learning machine included in the time determination unit to learn according to the second embodiment of the present invention.

With reference to FIGS. 13 and 14, a method of determining a whole-state observation time by the time determination unit 503 according to the second embodiment is described.

The time determination unit 503 includes a known learning machine such as a Support Vector Machine (SVM), a perceptron, or a neural classifier. The time determination unit 503 uses the learning machine to determine a time Tp at which an angular difference Δϕ(t) is locally minimum.

For preparation for the time Tp determination, the learning machine gathers and learns, as positive examples, a large number of waveforms of an angular difference Δϕ(t) in an observation time width Tw having a time Tp as a center time. FIG. 13 is a graph showing an example of the positive example used in the learning. In the positive examples, within an observation time width Tw, values of angular differences Δϕ(t) are continuously decreased from a start time of the observation time width Tw to the minimum decrease time period Td. Furthermore, the angular difference Δϕ(t) is locally minimum at the center time (time Tp) of the observation time width Tw, and a local minimum value among the angular differences Δϕ(t) is equal to or smaller than the predetermined threshold value ϕth.

The learning machine gathers and learns also a large number of negative examples. FIG. 14 is a graph showing an example of an angular difference Δϕ(t) showing a negative example. The negative examples refer to all waveforms of an angular difference Δϕ(t), except the positive examples. For example, the example in FIG. 14 does not satisfy conditions of positive examples under which, within a target observation time width Tw, values of angular differences Δϕ(t) are continuously decreased from a start time of the observation time width Tw to the minimum decrease time period Td. Furthermore, the angular difference Δϕ(t) is locally minimum at the center time of the observation time width Tw, and a local minimum value among the angular differences Δϕ(t) is equal to or smaller than the predetermined threshold value ϕth.

The time determination unit 503 shifts the predetermined observation time width Tw in a time axis direction, overlapping the observation time widths Tw each other. Thereby, the time determination unit 503 sequentially samples values of angular differences Δϕ(t) included in each observation time width Tw. The time determination unit 503 outputs the angular differences Δϕ(t) included in the target observation time width Tw, to the above-described learning machine. If the output of the learning machine is a positive example, the time determination unit 503 determines the center time of the observation time width Tw as a time Tp. On the other hand, if the output of the learning machine is a negative example, the time determination unit 503 does not determine a time Tp. After that, in the same manner as described in the first embodiment, the time determination unit 503 determines whether or not there is any time Ta. If there is a time Ta, the time determination unit 503 outputs the time Tp as a whole-state observation time.

Figure 15:
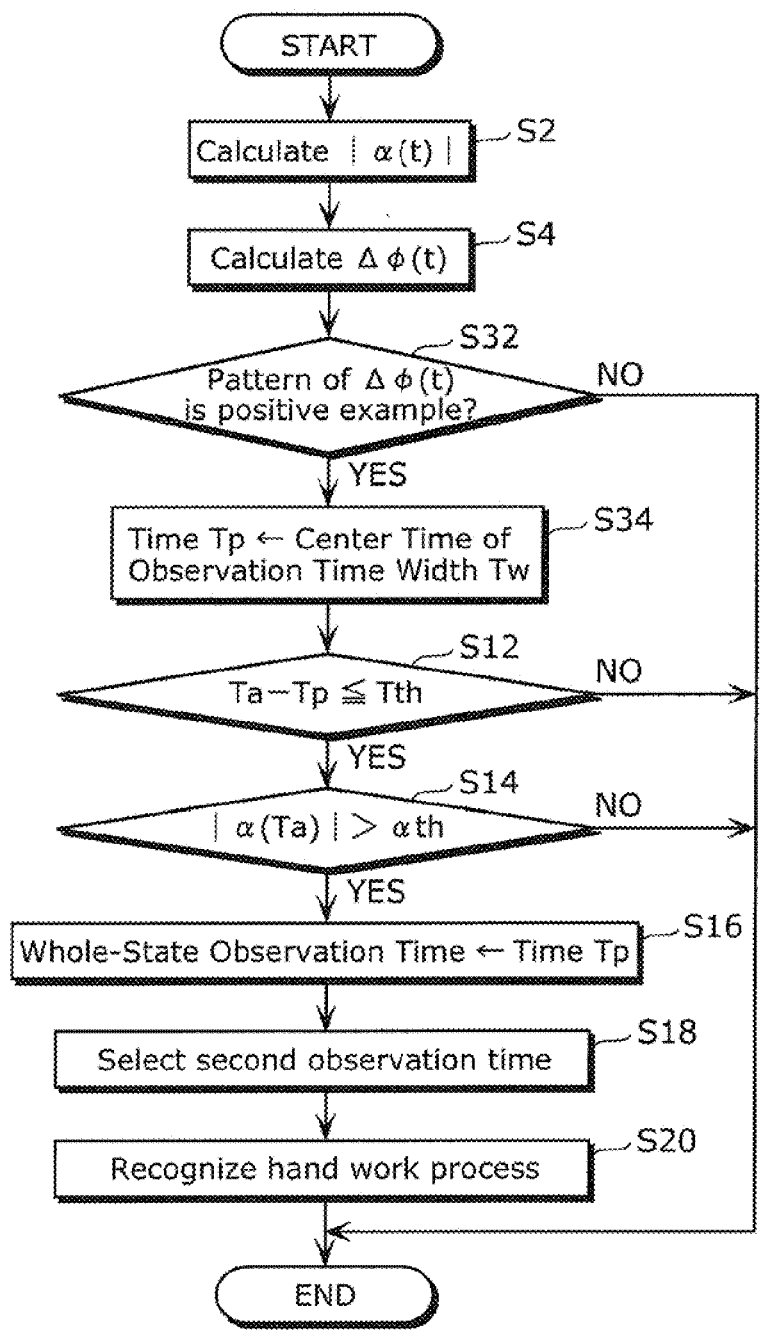
FIG. 15 is a flowchart of processing performed by a hand work recognition device according to the second embodiment of the present invention.

The following describes a flow of the processing performed by the hand work recognition device in the hand work recognition system having the above structure with reference to FIG. 15.

The processing performed by the hand work recognition device according to the second embodiment differs from the processing performed by the hand work recognition device shown in FIG. 10 according to the first embodiment in that the steps S6 to S10 are replaced by steps S32 and S34 described below. Except these steps, the second embodiment is the same as the first embodiment. Therefore, the details are not repeated in the second embodiment.

The time determination unit 503 shifts the predetermined observation time width Tw in a time axis direction, overlapping the observation time widths Tw each other. Sequentially, the time determination unit 503 samples values of angular differences Δϕ(t) included in each observation time width Tw. The time determination unit 503 outputs the angular differences Δϕ(t) included in a target observation time width Tw into the above-described learning machine. If the output of the learning machine is a positive example (YES at S32), the time determination unit 503 determines the center time of the observation time width Tw as a time Tp (S34). On the other hand, if the output of the learning machine is a negative example (NO at S32), the time determination unit 503 does not determine a time Tp.

With the above structure, as shown in (a) in FIG. 11, the second sensor 202 outputs consecutive second observation values. On the other hand, according to each of the whole-state observation times Tp determined by the whole-state observation time determination unit 303, the observation value selection unit 304 selects a second observation value to be an input of the process recognition unit 305 as shown in (b) in FIG. 11. The whole-state observation time determination unit 303 determines each of the whole-state observation times Tp in real time by the above-described processing based on changes of an angular difference $\Delta\phi(t)$ and an acceleration magnitude $|\alpha(t)|$. Thereby, when the user carefully performs hand work such as cooking, cleaning, and laundry in daily life, it is possible to extract only a second observation value(s) having a high possibility of occurring at a boundary between work processes, such as a start, an end, or a turning point of an action of a user's hand.

The process recognition unit 305 calculates, only for a received second observation value(s), a relevance between the second observation value (image, for example) and pieces of knowledge data regarding image features which are previously learned from respective processes in the user's hand work. Then, the process recognition unit 305 determines, as a hand work process, a hand work process of a piece of the knowledge data to which a target second observation value is most related. The process recognition unit 305 outputs the determined hand work process as a recognition result. Therefore, the process recognition unit 305 evaluates a part of all second observation values which are generated by the second sensor 202, which makes it possible to significantly reduce a calculation amount required to evaluate the learned knowledge for each input observation value. As a result, it is possible to increase a processing speed, and thereby extracting a user's action or an object promptly.

Although the above has described the embodiments of the hand work recognition system according to the present invention, the present invention is not limited to these embodiments.

For example, it has been described in the above-described embodiments that processes in hand work performed by a user is recognized. However, a target to be recognized is not limited to processes in hand work, but processes in any work associated with movements of a user's hand. For instance, the second sensor 202 may capture an image of a whole-state user. Thereby, a second observation value is compared to pieces of knowledge data of user's actions associated with user's hand movements, thereby recognizing user's actions. It is also possible to capture an image of legs of a user by the second sensor 202. Thereby, a second observation value is compared to pieces of knowledge data of user's work processes using legs which are associated with user's leg movements, thereby recognizing a process in the user's leg work.

It should also be noted that the observation value selection unit 304 may select not only a second observation value, but also a first observation value observed at the same whole-state observation time as that of the second observation value.

It should also be noted that the observation value selection unit 304 may select not only a second observation value of a whole-state observation time Tp, but also second observation values of pictures prior and subsequent to the whole-state observation time Tp.

It should also be noted that it has been described that the whole-state observation time determination unit 303 determines the time Tp to be a whole-state observation time, but may determine the time Ta to be a whole-state observation time.

It should also be noted that it has been described that the learning machine in the time determination unit 503 according to the second embodiment determines the time Tp based only on angular differences $\Delta\phi(t)$. However, the time Tp determination may be performed by sampling $|\alpha(t)|$ in a target observation time width Tw to be used together with the angular differences $\Delta\phi(t)$.

It should also be noted that it has been described in the above embodiments that the processing of the present invention is performed for cooking work at general home as an example, but the present invention is not limited to the above. In other words, as long as the recognized hand work is carefully performed by a person, the present invention can be used for various hand work other than the work at general home. For example, the present invention can be performed for assembly work of home appliances in production sites. Thereby, results of work recognition can be used to manage and efficiently perform production processes. For example, in the case where a production site is captured and managed by a camcorder, work recognition results are assigned as indexes to respective images in daily-accumulated video. Thereby, when the accumulated video is later analyzed off-line, it is possible to speedily access a desired work scene.

It should also be noted that it has been described in the above embodiments that the second sensor is a camera capturing images, but the second sensor may be a microphone collecting sound resulting from hand work processes. In the above case, the process recognition unit 305 calculates a relevance between a current sound and previously-learned pieces of knowledge data of user's hand work processes. Thereby, the process recognition unit 305 determines, as a hand work process, a hand work process associated with a piece of knowledge data to which the current sound is most relevant. The process recognition unit 305 outputs the determined hand work process as a recognition result. Furthermore, the second sensor may include: a camera capturing images of hand work processes; and a microphone gathering sound resulting from the hand work processes. In the above case, the process recognition unit 305 may perform its processing based on a relevance between (i) current image and sound and (ii) previously-learned pieces of knowledge data of image features and audio features of user's hand work processes. More specifically, it is possible to output, as a recognition result, a hand work process associated with a piece of knowledge data to which the current image and sound are most relevant.

It should also be noted that, if work is performed by both hands, it is also possible to attach a plurality of the first sensors 201 to the left and right hands, respectively, and to provide a plurality of the whole-state observation time determination units 303 for the left and right hands, respectively. Thereby, it is possible to increase second observation values to be selected.

It should also be noted that it is also possible that a three-directional gyro-sensor or an angular velocity sensor is integrated to the triaxial acceleration sensor 401, in order to estimate an attitude of the angular velocity sensor. Thereby, the magnitude estimation unit 501 can estimate $|\alpha(t)|$ more correctly, and the time determination unit 503 can perform the determination at a higher accuracy.

Figure 16:
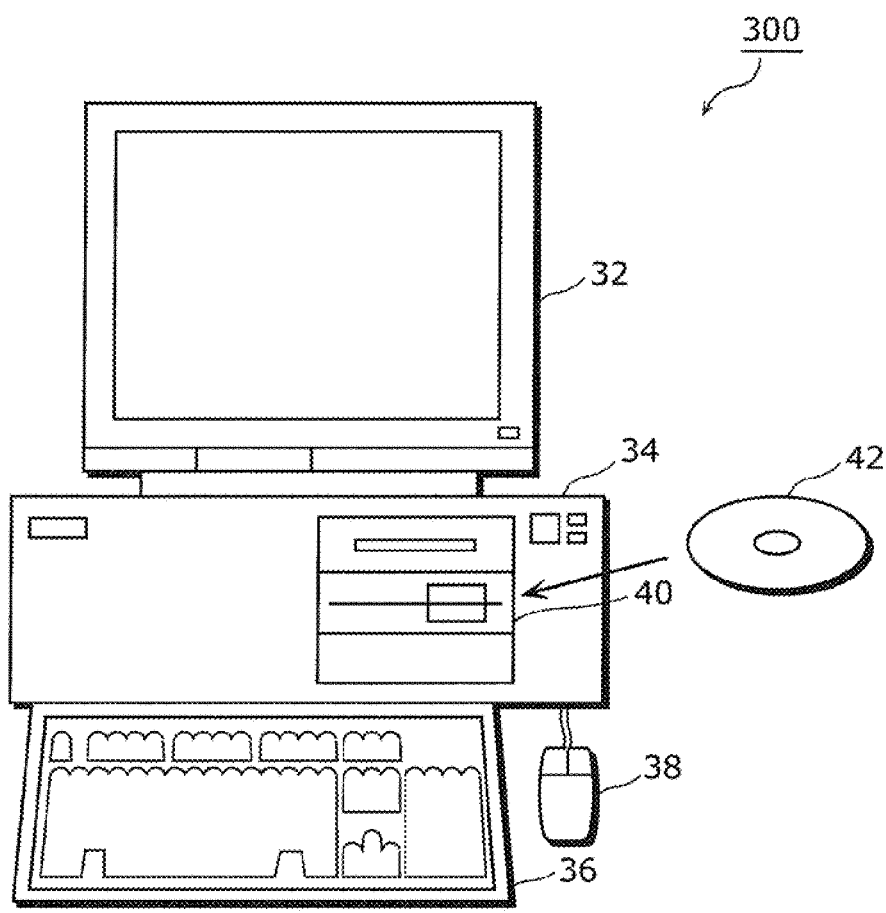
FIG. 16 is an external view of the hand work recognition device according to the first or second embodiment of the present invention.

It should also be noted that the hand work recognition device 300 described in the first and second embodiments can be implemented as a computer. As shown in FIG. 16, the hand work recognition device 300 includes: a computer 34; a keyboard 36 and a mouse 38 which are used to give instructions to the computer 34; a display 32 for presenting information such as operation results of the computer 34; a Compact Disc-Read Only Memory (CD-ROM) device 40 for reading a program executed by the computer 34; and a communication modem (not shown).

The program for recognizing processes in hand work is stored in the computer-readable medium CD-ROM 42, and read by the CD-ROM device 40. Or, the program is read by the communication modem via a computer network 26.

Figure 17:
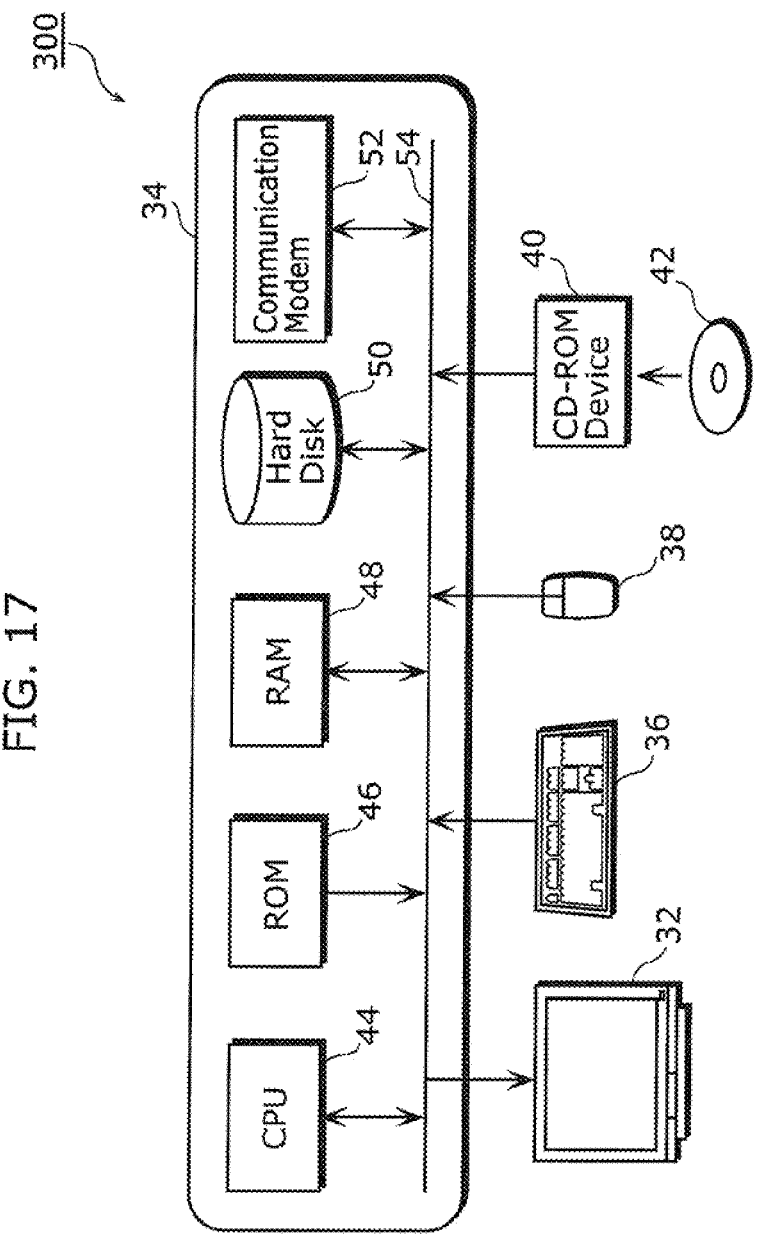
FIG. 17 is a block diagram showing a hardware structure of the hand work recognition device according to the first or second embodiment of the present invention.
Figure 18:
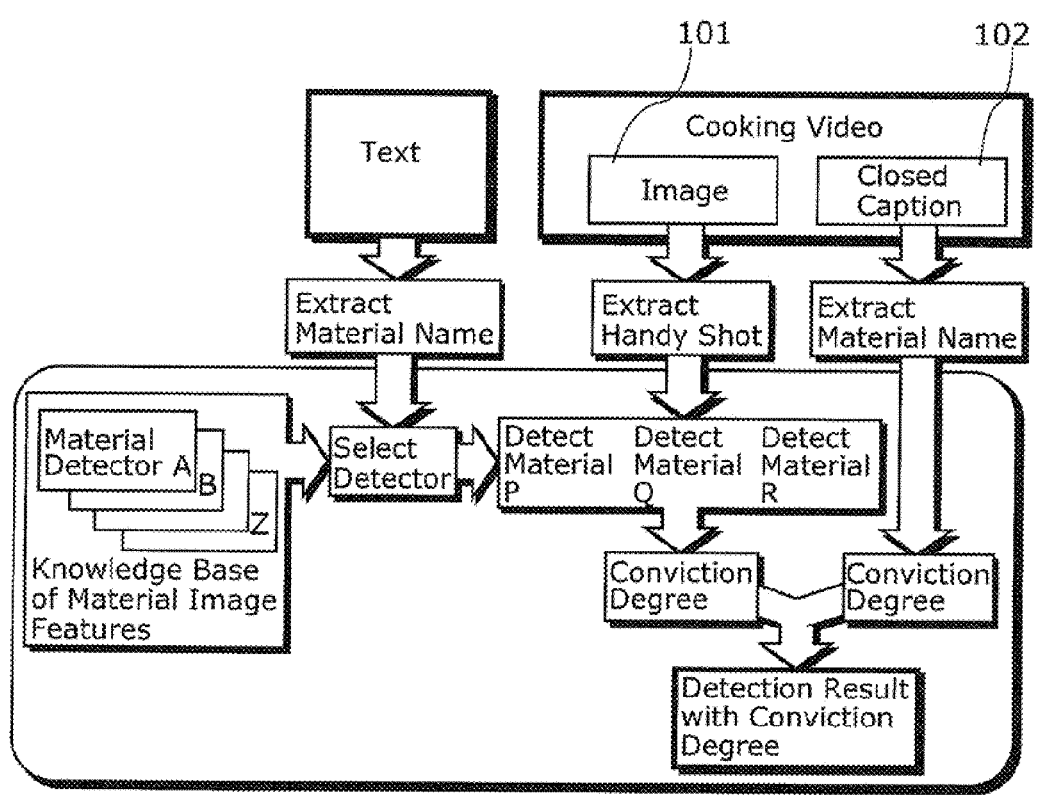
FIG. 18 is a diagram showing a summary of processing for recognizing a process in hand work performed by a person, which is disclosed in Non-Patent Reference 1.

FIG. 17 is a block diagram showing a hardware structure of the hand work recognition device 300. The computer 34 includes a Central Processing Unit (CPU) 44, a Read Only Memory (ROM) 46, a Random Access Memory (RAM) 48, a hard disk 50, a communication modem 52, and a bus 54.

The CPU 44 executes the program that is read via the CD-ROM device 40 or the communication modem 52. The ROM 46 stores programs and data required to operate the computer 34. The RAM 48 stores data such as parameters used in executing the programs. The hard disk 50 stores the programs, data, and the like. The communication modem 52 communicates with other computers via the computer network 26. The bus 54 connects the CPU 44, the ROM 46, the RAM 48, the hard disk 50, the communication modem 52, the display 32, the keyboard 36, the mouse 38, and the CD-ROM device 40 to one another.

It should be noted that a part or all of the structural elements included in each of the above devices may be implemented into a single Large Scale Integration (LSI). The system LSI is a super multi-function LSI that is a single chip into which a plurality of structural elements are integrated. More specifically, the system LSI is a computer system including a microprocessor, a ROM, a RAM, and the like. The RAM holds a computer program. The microprocessor executes the computer program to cause the system LSI to perform its functions.

It should also be noted that a part or all of the structural elements included in each of the above devices may be implemented into an Integrated Circuit (IC) card or a single module which is attachable to and removable from the device. The IC card or the module is a computer system including a microprocessor, a ROM, a RAM, and the like. The IC card or the module may include the above-described super multi-function LSI. The microprocessor executes the computer program to cause the IC card or the module to perform its functions. The IC card or the module may have tamper resistance.

It should also be noted that the present invention may be the above-described method. The present invention may be a computer program causing a computer to execute the method, or digital signals indicating the computer program.

It should also be noted that the present invention may be a computer-readable recording medium on which the computer program or the digital signals are recorded. Examples of the computer-readable recording medium are a flexible disk, a hard disk, a Compact Disc (CD)-ROM, a magnetooptic disk (MO), a Digital Versatile Disc (DVD), a DVD-ROM, a DVD-RAM, a BD (Blue-Ray®) Disc), and a semiconductor memory. The present invention may be digital signals recorded on the recording medium.

It should also be noted in the present invention that the computer program or the digital signals may be transmitted via an electric communication line, a wired or wireless communication line, a network represented by the Internet, data broadcasting, and the like.

It should also be noted that the present invention may be a computer system including a microprocessor operating according to the computer program and a memory storing the computer program.

It should also be noted that the program or the digital signals may be recorded onto the recording medium to be transferred, or may be transmitted via a network or the like, so that the program or the digital signals can be executed by a different independent computer system.

It should also be noted that the above-described embodiments and their variations may be combined.

The disclosed embodiments are merely exemplary and do not limit the present invention. The scope of the present invention is indicated not by the above description but by the appended claims. Accordingly, all modifications are intended to be included within the same meanings and the scope of the claims.

The hand work recognition system according to the present invention has a capability of recognizing user's work processes at a high speed. The hand work recognition system can generate operation triggers and the like for white appliances and domestic work supporting robots. In addition, the hand work recognition system can be applied to recognize processes in work such as cleaning and laundry, and also to monitor assembly work in factories, for example.

NUMERICAL REFERENCES 101 image
102 closed caption
201 first sensor
202 second sensor
203 information provision device
300 hand work recognition device
303 whole-state observation time determination unit
304 observation value selection unit
305 process recognition unit
401 triaxial acceleration sensor
402, 504 wireless data transmitting/receiving unit
403 power source unit
501 magnitude estimation unit
502 angular difference calculation unit
503 time determination unit

The invention claimed is:
1. A work recognition device, comprising:
a whole-state observation time determination unit configured to determine, as a whole-state observation time, from among observation times of a plurality of first observation values generated by a speed sensor to represent respective movements of a hand of a user in chronological order, an observation time of observing a first observation value representing a predetermined movement of the hand, based on magnitudes of the plurality of first observation values and an angular difference between the plurality of first observation values; and
an observation value selection unit configured to select a second observation value corresponding to the whole-state observation time determined by the whole-state observation time determination unit, from among a plurality of second observation values generated by an imaging unit to represent respective states in work of the user in chronological order,
wherein the whole-state observation time determination unit includes:
a magnitude estimation unit configured to estimate a magnitude of an acceleration that is obtained by subtracting a gravity acceleration from each of the accelerations generated by the speed sensor;

an angular difference calculation unit configured to calculate, for each of the accelerations generated by the speed sensor, an angle between (a) one acceleration at a corresponding observation time and (b) another acceleration at an observation time prior to the corresponding observation time; and a time determination unit configured to determine, as the whole-state observation time, the corresponding observation time, when (a) a magnitude of the one acceleration which is estimated by the magnitude estimation unit and (b) the angle calculated by the angular difference calculation unit show a predetermined pattern.

2. The work recognition device according to claim 1, further comprising a process recognition unit configured to recognize a process in the work, by comparing the second observation value selected by the observation value selection unit to pieces of knowledge data associated with respective processes in the work, in each of the respective processes the user is performing the predetermined movement of the hand.

3. The work recognition device according to claim 1, wherein the whole-state observation time determination unit is configured to determine, as the whole-state observation time, a time having a local minimum value of an amount of a change between the plurality of first observation values.

4. The work recognition device according to claim 1, wherein the whole-state observation time determination unit is configured to determine the whole-state observation time based on magnitudes of at least a part of the plurality of first observation values, the at least the part being generated during a time period after a first time until a predetermined time, and the first time being a time having a local minimum value of an amount of a change between the plurality of the first observation values.

5. The work recognition device according to claim 4, wherein the whole-state observation time determination unit is configured to determine, as the whole-state observation time, a time closest to the first time from among times having local maximum values or maximum values of the magnitudes of the at least a part of the plurality of first observation values generated during the time period after the first time until the predetermined time.

6. The work recognition device according to claim 1, wherein the speed sensor is a triaxial acceleration sensor that generates accelerations in chronological order as the plurality of first observation values.

7. The work recognition device according to claim 6, wherein the user wears the speed sensor on a dominant hand of the user.

8. The work recognition device according to claim 6, wherein the whole-state observation time determination unit is configured to determine, as the whole-state observation time, based on the plurality of the first observation values generated in chronological order, an observation time having a local minimum value representing a change of a direction of the hand, when a magnitude of an acceleration of the hand becomes locally maximum after the observation time having the local minimum value.

9. The work recognition device according to claim 1, wherein the time determination unit is configured to determine, as the whole-state observation time, a time at which (b) the angle calculated by the angular difference calculation unit approaches asymptotically to 0 degrees, when (a) the magnitude of the one acceleration which is estimated by the magnitude estimation unit becomes locally maximum within a predetermined time period immediately after the time.

10. The work recognition device according to claim 9, wherein the time determination unit is configured to determine the time at which (a) the angle calculated by the angular difference calculation unit approaches asymptotically to 0 degrees, using a learning machine that learns angles at respective times at which the angles approaches asymptotically to 0 degrees.

11. The work recognition device according to claim 1, wherein the magnitude estimation unit is configured to approximate magnitudes of accelerations that are obtained by subtracting a magnitude of the gravity acceleration from each of the magnitudes of the accelerations generated by the speed sensor.

12. The work recognition device according to claim 1, wherein the imaging unit is a camera that captures an image of a range of a process in the work of the user.

13. A work recognition system that recognizes processes in work performed by a user, the work recognition system comprising:

a speed sensor that generates, in chronological order, a plurality of first observation values representing respective movements of a hand of the user performing the work;

an imaging unit configured to generate, in chronological order, a plurality of second observation values representing respective states in the work; and a work recognition device that recognizes a process in the work based on the plurality of first observation values generated in chronological order and the plurality of second observation values generated in chronological order, wherein the work recognition device includes:

a whole-state observation time determination unit configured to determine, as a whole-state observation time, from among observation times of a plurality of first observation values generated in chronological order, an observation time of observing a first observation value representing a predetermined movement of the hand, based on magnitudes of the plurality of first observation values and an angular difference between the plurality of first observation values;

an observation value selection unit configured to select a second observation value corresponding to the whole-state observation time determined by the whole-state observation time determination unit, from among a plurality of second observation values generated in chronological order; and a process recognition unit configured to specify a process in the work, by comparing the second observation value selected by the observation value selection unit to pieces of knowledge data associated with respective processes in the work, in each of the respective processes the user performing the predetermined movement of the hand, wherein the whole-state observation time determination unit includes:

a magnitude estimation unit configured to estimate a magnitude of an acceleration that is obtained by subtracting a gravity acceleration from each of the accelerations generated by the speed sensor;

an angular difference calculation unit configured to calculate, for each of the accelerations generated by the speed sensor, an angle between (a) one acceleration at a corresponding observation time and (b) another acceleration at an observation time prior to the corresponding observation time; and a time determination unit configured to determine, as the whole-state observation time, the corresponding observation time, when (a) a magnitude of the one acceleration which is estimated by the magnitude estimation unit and (b) the angle calculated by the angular difference calculation unit show a predetermined pattern.

14. A work recognition method of recognizing, by using a computer, processes in work performed by a user, the work recognition method comprising:
  determining, as a whole-state observation time, from among observation times of a plurality of first observation values generated by a speed sensor to represent respective movements of a hand of the user in chronological order, an observation time of observing a first observation value representing a predetermined movement of the hand, based on magnitudes of the plurality of first observation values and an angular difference between the plurality of the first observation values;
  selecting a second observation value corresponding to the whole-state observation time determined in the determining, from among a plurality of second observation values generated by an imaging unit to represent respective states in work of the user; and
  specifying a process in the work, by comparing the second observation value selected in the selecting to pieces of knowledge data associated with respective processes in the work, in each of the respective processes the user performing the predetermined movement of the hand,
  wherein the determining step includes:
  estimating a magnitude of an acceleration that is obtained by subtracting a gravity acceleration from each of the accelerations generated by the speed sensor;
  calculating, for each of the accelerations generated by the speed sensor, an angle between (a) one acceleration at a corresponding observation time and (b) another acceleration at an observation time prior to the corresponding observation time; and
  determining, as the whole-state observation time, the corresponding observation time, when (a) a magnitude of the one acceleration which is estimated in the estimating and (b) the angle calculated in the calculating show a predetermined pattern.

15. A computer program which is recorded on a non-transitory computer-readable recording medium for use in a computer and is used for recognizing processes in work performed by a user, the computer program causing the computer to execute:
  determining, as a whole-state observation time, from among observation times of a plurality of first observation values generated by a speed sensor to represent respective movements of a hand of the user in chronological order, an observation time of observing a first observation value representing a predetermined movement of the hand, based on magnitudes of the plurality of first observation values and an angular difference between the plurality of first observation values;
  selecting a second observation value corresponding to the whole-state observation time determined in the determining, from among a plurality of second observation values generated by an imaging unit to represent respective states in work of the user; and
  specifying a process in the work, by comparing the second observation value selected in the selecting to pieces of knowledge data associated with respective processes in the work, in each of the respective processes the user performing the predetermined movement of the hand,
  wherein the determining step includes:
  estimating a magnitude of an acceleration that is obtained by subtracting a gravity acceleration from each of the accelerations generated by the speed sensor;
  calculating, for each of the accelerations generated by the speed sensor, an angle between (a) one acceleration at a corresponding observation time and (b) another acceleration at an observation time prior to the corresponding observation time; and
  determining, as the whole-state observation time, the corresponding observation time, when (a) a magnitude of the one acceleration which is estimated in the estimating and (b) the angle calculated in the calculating show a predetermined pattern.

* * * * *